United States Patent
Brown et al.

(10) Patent No.: US 7,103,207 B2
(45) Date of Patent: Sep. 5, 2006

(54) SPECTRAL ASSESSMENT OF FRUIT

(75) Inventors: Peter Gary Brown, Mount Egerton (AU); Colin Victor Greensill, Parkhurst (AU); Kerry Brian Walsh, Yeppoon (AU)

(73) Assignees: Color Vision Systems PTD Ltd., Bacchus Marsh (AU); Central Queensland University, North Rockhampton (AU)

( * ) Notice: Subject to any disclaimer, the term of this patent is extended or adjusted under 35 U.S.C. 154(b) by 700 days.

(21) Appl. No.: 10/220,739

(22) PCT Filed: Mar. 7, 2001

(86) PCT No.: PCT/AU01/00242

§ 371 (c)(1),
(2), (4) Date: Nov. 14, 2002

(87) PCT Pub. No.: WO01/67073

PCT Pub. Date: Sep. 13, 2001

(65) Prior Publication Data

US 2003/0149544 A1   Aug. 7, 2003

(30) Foreign Application Priority Data

Mar. 7, 2000   (AU) .................................. PQ6071

(51) Int. Cl.
*G06K 9/00*   (2006.01)
(52) U.S. Cl. ...................... 382/141; 382/143; 382/149; 348/89; 348/108
(58) Field of Classification Search ................ 382/141, 382/149, 268, 143, 274; 356/73, 73.1; 348/86, 348/89, 92, 108
See application file for complete search history.

(56) References Cited

U.S. PATENT DOCUMENTS

| 4,515,275 | A | | 5/1985 | Mills et al. |
| 4,718,223 | A | * | 1/1988 | Suzuki et al. ............... 56/328.1 |
| 4,741,042 | A | | 4/1988 | Throop et al. |
| 5,089,701 | A | * | 2/1992 | Dull et al. ............. 250/339.08 |
| 5,164,795 | A | | 11/1992 | Conway |
| 5,660,676 | A | * | 8/1997 | Brooks ....................... 156/361 |
| 5,708,271 | A | * | 1/1998 | Ito et al. ................. 250/339.11 |
| 5,845,002 | A | * | 12/1998 | Heck et al. ................. 382/110 |
| 5,926,262 | A | * | 7/1999 | Jung et al. ..................... 356/73 |
| 6,075,594 | A | * | 6/2000 | Thomas et al. ............. 356/328 |
| 6,153,253 | A | * | 11/2000 | Affeldt et al. ................. 427/8 |
| 6,512,577 | B1 | * | 1/2003 | Ozanich ....................... 356/73 |

FOREIGN PATENT DOCUMENTS

| EP | 0 939 316 A2 | 9/1999 |
| JP | 11-173985 A | 7/1999 |
| WO | WO 96/27783 | 9/1996 |

* cited by examiner

*Primary Examiner*—Samir Ahmed
*Assistant Examiner*—Yosef Kassa
(74) *Attorney, Agent, or Firm*—Stites & Harbison PLLC; Ross F. Hunt, Jr.

(57) ABSTRACT

Apparatus for the spectral assessment of fruit includes a sensor head (10) positioned adjacent a near infrared light source (11). The sensor head is coupled to a spectrometer via fibre optics (30). The sensor head is positioned close to the periphery of fruit substantially parallel with the light from the light source so that the fibre optics sense only the internally reflected or refracted light emanating from the fruit.

15 Claims, 3 Drawing Sheets

SPECTRAL ASSESSMENT OF FRUIT

INTRODUCTION

This invention relates to spectral assessment of fruit and in particular relates to an optical configuration that can be used to spectrally assess characteristics of fruit. The invention also embraces an assembly that can spectrally assess fruit as it is transported on a conveyor.

BACKGROUND OF THE INVENTION

The monitoring of eating quality of fruit and vegetables by objective methods is usually destructive and slow (eg squeezing juice to measure Brix). There is a need to be able to rapidly and non-invasively evaluate the internal quality of fresh fruit and vegetables which may enter the fresh market channels or be used for processing. Near infra-red spectroscopy (NIRS), nuclear magnetic resonance (NMR), and acoustic techniques all offer potential for the non-invasive assessment of the internal composition of intact fruit. Of the above NIRS is the most advanced technique with regard to instrumentation, applications, accessories and chemometric software packages, and with respect to cost and speed of operation.

Near infra-red light (NIR) is a small part of the spectrum of electromagnetic radiation—which starts at high-energy waves such as x-rays, through the visible spectrum, to low energy waves such as microwaves and radio waves. NIR is next to the visible portion of light and is a natural part of sunlight. NIR is typically defined as radiation of wavelengths 700–2500 nm, which is invisible to the human eye.

Specific molecules can absorb specific wavelengths. This characteristic is useful in the identification and quantification of a given compound. Absorption of ultraviolet and visible light is associated with the transition of electrons between orbitals in an atom or molecule. Absorption of infra-red radiation by biological material principally involves the rotation and stretching of N—H, C—H and O—H bonds. These bonds are associated with constituents of interest to fruit quality evaluation, including sugar, starch, protein, lipids and water. The infra-red absorption spectrum is commonly used by organic chemists to fingerprint organic molecules. However, ultraviolet, visible and infra-red radiation have poor penetration through bulk tissue. In essence, techniques relying on these wavelengths are useful for solutions or for surface studies. Fortunately, the near infra-red region of the electromagnetic spectrum does penetrate relatively well through bulk biological material, and this region also carries an 'echo' of information of the infrared absorption spectrum. Unfortunately, the second and third overtone absorption bands which occur in the near infra-red region are weak and broad, and thus NIRS have been a 'slow starter' relative to other techniques, and are only now achieving widespread commercial application.

NIRS technology has been trialed in horticultural applications for over 20 years. However, recent developments in fibre optics, array detectors computing power of PCs and of software capable of carrying out the complex statistical mathematics has made application to inline fruit packing possible.

Past proposals involve the use of either reflectants spectroscopy, with a detector viewing an illuminated area of the fruit, or partial transmittance spectroscopy with the detector mounted at an angle away from the detector. The detector is commonly an array spectrometer, allowing spectral analysis to determine characteristics of the fruit.

Past proposals involve use of tungsten halogen light sources as strong emitters of NIR or NIR emitting diode lasers, at wavelengths chosen relative to the band assignments of the character of interest. For example, U.S. Pat. No. 5,708,271 employs NIR lasers directed at the center of the fruit at an angle of other than 0° and 180°, and commonly 40° to 60°, to the line of the detector and fruit center.

SUMMARY OF THE INVENTION

In essence the subject invention has means to pass fruit past a sensor head positioned adjacent a near infra-red light source, the sensor head being coupled to a spectrometer via fibre optics characterised in that the sensor head is positioned substantially parallel with the light from the light source, the fibre optics sensing only the internally reflected or refracted light emanating from the fruit.

DESCRIPTION OF THE DRAWINGS

Embodiments of the present invention will now be described by way of example only with reference to their accompanying drawings in which.

DESCRIPTION OF THE PREFERRED EMBODIMENT

Figure 1:
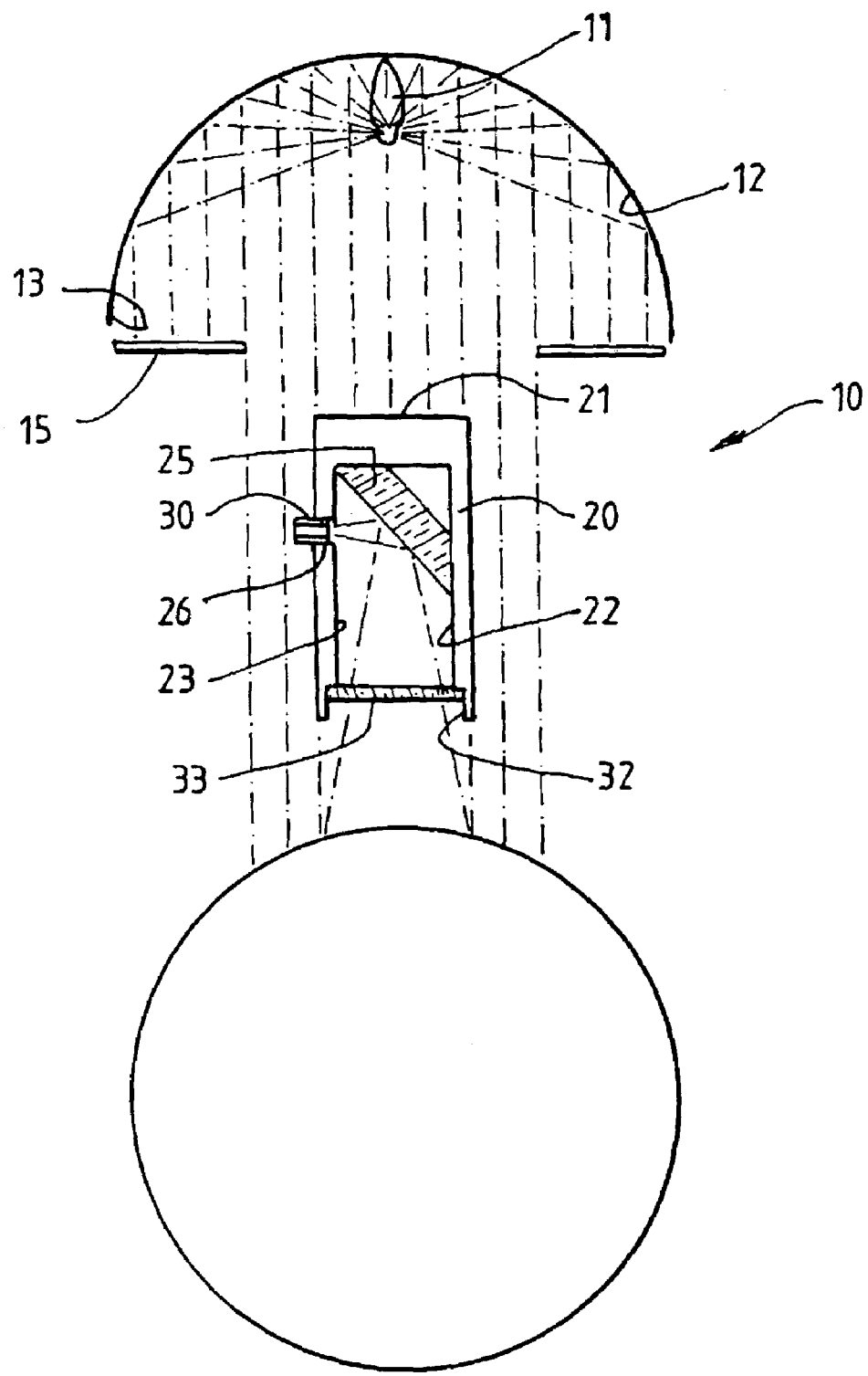
FIG. 1 is a schematic illustration of one embodiment of an optical sensing unit.
Figure 2:
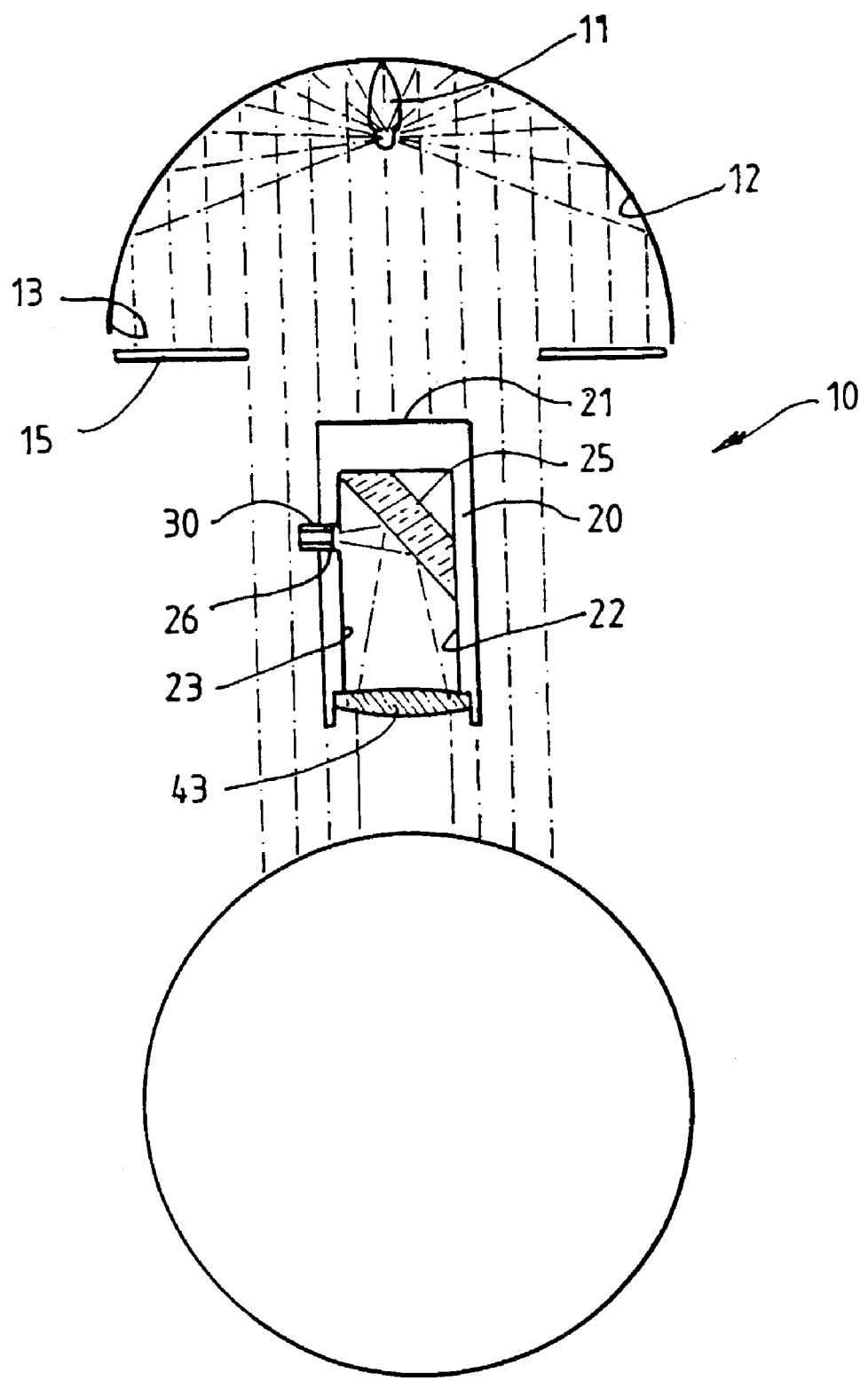
FIG. 2 is a schematic illustration of another embodiment of an optical light sensing unit.

The FIGS. 1 and 2 show two schematic illustrations of optical sensing units that are used to spectrally assess the characteristics of melons. The melons are placed on a cup that forms part of a conveyor. The sensing unit 10 is mounted on a support structure (not shown) to be in close proximity to the periphery of the melons as they pass the optical unit. The optical unit has an incandescent light source 11, namely tungsten halogen, positioned centrally of a parabolic reflector 12. The mouth 13 of the reflector 12 is provided with an annular aperture 15 with a circular opening and the geometry of the reflector 12 is designed so that light leaves the reflector 12 as a collimated beam to effectively impinge radially on the fruit. A probe in the form of a cylinder 20 having a closed end 21 and an open mouth 22 is positioned with the mouth 22 of the cylinder 20 approximately 20 to 30 millimetres from the periphery of the melon.

The probe is coated in a suitable matt black non light-reflective coating and includes a cylindrical chamber 23 in which is mounted a reflective mirror 25 at one end extending at 45 degrees to the axis of the cylinder 20. The wall of the cylinder is provided with a small aperture 26 into which are housed the fibre ends 30 of a fibre optic cable (not shown) that extends back to a spectrometer (not shown). The mouth 22 of the probe has a stepped recess 32 which houses a plain glass window 33. The probe has the effect of blocking some of the parallel beams of light from the parabolic reflector 12 thus leaving a shadow on the surface of the fruit beneath the probe. The light outside the shadow hits the fruit as a collimated beam and then as it enters the fruit it becomes refracted and reflected by the interior of the fruit. The reflected and refracted light from the shaded area can be picked up by a highly sensitive sensor after reflecting off the surface of the internal mirror 15 and being transmitted to be picked up by the fibre optic cable.

A similar optical unit is shown in FIG. 2 except hat in that embodiment the plain glass window 33 has been replaced by a convex lens 43 that has the effect of making the radius of the viewed area independent of the distances from probe to fruit surface. In all other aspects this unit is the same as the unit shown in FIG. 1.

The signal picked up by the optical unit can be passed to a spectrometer which can then carry out the analysis necessary to determine various parameters of the fruit especially the sweetness of the fruit.

An important advantage that flows from this development is the capacity to speedily view all fruit in a batch by passing each piece of fruit past the optical unit. For some years it has been known to provide fruit handling equipment whereby fruit of various types is positioned individually on a carrying cup attached to a chain conveyor. The fruit can be rotated past a photographic zone that would contain a CCD camera. The camera would be able to note the size, colour and blemishes on the fruit. This information would be fed to a computer which then orchestrates ejection means to cause the fruit to be ejected from the conveyor into bins categorised by size, weight or colour. When equipment of this kind is used with the optical sensing units described above it will be understood that the optical sensing units will be mounted on means that incorporates some form of servo motor control that allows the position of the head relative to the fruit to vary in dependence of the size of the fruit. It has been discovered that 20 millimetres is the optimum distance from the lens of the unit to the periphery of the fruit and to ensure that the unit remains at this optimum distance the computer will note the size of the fruit and then instruct the servo motor to move the head to ensure there is always a gap of approximately 20 millimetres.

It is however understood that there are other ways of accommodating variations in fruit sizes that would not require the sophistication of computerised controlled movement of the optical head.

The similar optical unit shown in FIG. 2 has the advantage that the fruit to sensor distance is less critical. Provided the fruit size does not vary by more that approximately 40 millimetres then this sensor could be mounted in a fixed position.

Figures 3, 4:
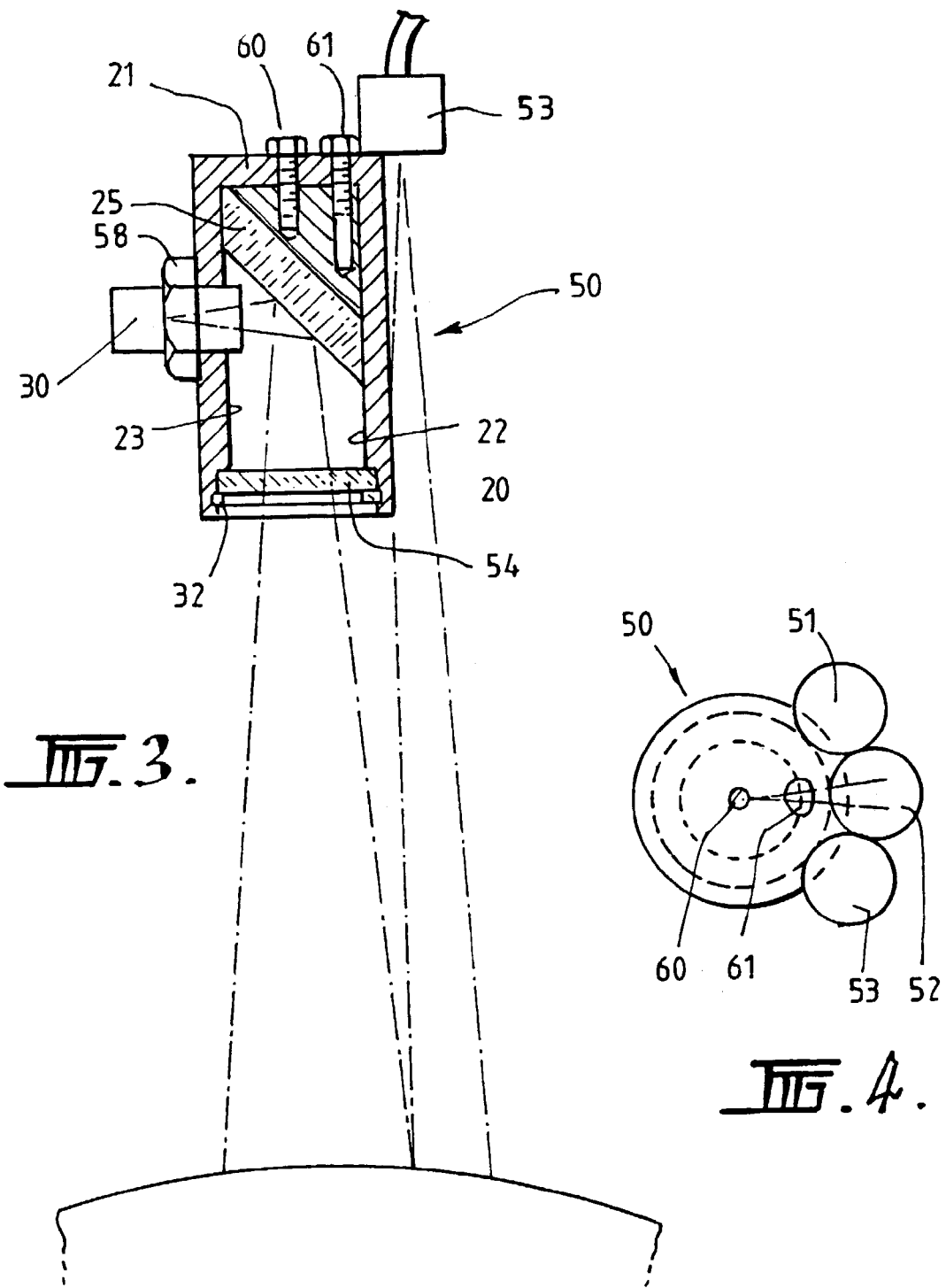
FIG. 3 is a cross sectional view of a sensing unit in accordance with a third embodiment.
FIG. 4 is a plan view of the unit of FIG. 3.

In a third embodiment illustrated in FIGS. 3 and 4, the incandescent light source 11 and parabolic reflector 12 are replaced by three lasers 51, 52 and 53 that are positioned about an arc on the right hand side of the cylinder 20 of the sensing unit 50 as shown in FIG. 4. The lasers 51, 52 and 53 are each configured to emanate a laser beam at wavelengths of 910 nm, 860 nm and 758 nm respectively. It is however understood that the NIR wavelengths can vary between 700 and 2500 nm.

As shown in FIG. 3, the optical sensing unit 50 includes the cylinder 20 with a closed end 21 and an open mouth 22. As in the earlier embodiments, the cylinder is coated in a suitable black non-light reflective coating and includes a cylindrical chamber 23 in which is mounted a reflective mirror 25 at one end extending at approximately 45° to the axis of the cylinder. As in the second embodiment, a lens 54 is positioned across the mouth of the open end of the cylinder. The fibre ends 30 of the optical fibre cable (not shown) are fed to the unit through a suitable coupling 58 that is screwed into the side of the cylinder. The fibre optic cable goes back to a spectrometer (not shown).

As shown in FIG. 3, the laser beams coming from the three lasers 51, 52 and 53 are directed against the sensing unit to cast a shadow on the surface of the fruit beneath the probe. Some of the laser beams directly contact the fruit and, although not shown in the drawings, it is understood that means such as fibre optics can be provided to control the direction of the light emanating from the lasers as collimated light directed to the fruit parallel to the sensor. The light that contact the fruit is refracted and reflected by the contents of the fruit in the same manner as the first embodiment and is then picked up via the mirror and reflected back to the spectrometer through the optical fibre cables. The mirror 25 is mounted on pivot bolt 60 which allows a small degree of adjustment to the mirror to alter its inclination to the axis of the cylinder. A second bolt 61 then locks the mirror in the selected position. The lens 54 assists in collecting the reflected signal from the surface of the fruit and directing that signal to the desired position on the mirror 25.

This embodiment has the advantage that the sensor can be further from the surface of the fruit and it is envisaged that the gap can be up to 50 mm. This is particularly useful when the sensor is used in a high speed assembly with fruit of differing sizes. It is understood that the number of lasers can vary and is it is envisaged that more than three could be provided in an arc around the upper edge of the sensor. The lasers are comparatively small measuring only 9 mm in diameter. The lasers could be positioned away from the sensor with fibre optics terminating at the head. It is further understood that the wavelengths emanating from the lasers would vary in dependence of the fruit character that is being spectrally assessed.

The method and apparatus described above has particular use as a means for measuring in a non-destructive manner the sugar content of fruit. For further disclosure of this measuring technique reference is made to the following patent literature: - U.S. Pat. Nos. 5,708,271, 5,324,945 and 5,089,701.

The invention claimed is:

1. Apparatus for the spectral assessment of fruit comprising a sensor head positioned adjacent a near infrared light source, the sensor head being coupled to a spectrometer via fibre optics, the sensor head being arranged to be positioned close to the periphery of fruit at least partially in the past of incident light from the light source to cast a shadow on the fruit, whereby the fibre optics sense the internally reflected or refracted light emanating from the shadow cast on the fruit.

2. Apparatus according to claim 1 wherein the light source comprises an incandescent light positioned in front of a parabolic reflector to provide a collimated beam.

3. The apparatus according to claim 1 wherein the light source comprises a plurality of lasers either positioned close to the sensor head or coupled to fibre optics terminating close to the sensor head.

4. The apparatus according to claim 1 wherein the lasers have collimated optics.

5. The apparatus according to claim 4 wherein the beam emanating from each laser is of a different wavelength.

6. The apparatus according to claim 5 wherein the wavelengths of the laser beams vary between 700 and 2500 nm.

7. The apparatus according to claim 6 wherein three lasers are used, the wavelengths of the light beams being respectively 910 nm, 860 nm and 758 nm.

8. The apparatus according to claim 1 wherein the sensor head is in the form of cylinder with an open end, the open end of the cylinder being positioned in close proximity to the periphery of the fruit, the cylinder containing a mirror so that light emanating from the shadow on the fruit is reflected by the mirror to be transferred by the fibre optics to an associated spectrometer.

9. The apparatus according to claim 8 wherein a lens is positioned across the open end of the cylinder.

10. Apparatus according to claim 1 comprising conveying means to support fruit to pass the sensor head in close proximity to the head.

11. The apparatus according to claim 10 wherein the spacings between the periphery of the fruit and the open end of the cylinder is between 20 and 50 mm.

12. The apparatus according to claim 1 wherein the sensor head is positioned in front of the light source and the incident light is a beam that casts the shadow on the fruit.

13. A method of a spectral assessment of fruit comprising passing the fruit past a sensor head positioned adjacent a near infrared light source, the sensor head being coupled to a spectrometer via fibre optics, the method comprising positioning the sensor head at least partially in the path of incident light from the light source to cast a shadow on the fruit, using the sensor head to pick up and transfer, the internally reflected or refracted light emanating from the shadow case on the fruit to the spectrometer via the fibre optics, and conducting a spectral analysis of the transferred light.

14. The method of claim 13 comprising placing the fruit on a conveyor and mounting the sensor head in close proximity above the periphery of the fruit.

15. The method of claim 13 comprising positioning the sensor head in front of the light source to cast a shadow on the fruit and conducting spectral analysis on the light emitted from the shadow.

* * * * *